US012303338B2

(12) United States Patent
Toporek et al.

(10) Patent No.: US 12,303,338 B2
(45) Date of Patent: May 20, 2025

(54) PLAN-SPECIFIC INSTRUMENT TEMPLATE FOR PERCUTANEOUS INTERVENTIONAL PROCEDURES

(71) Applicant: KONINKLIJKE PHILIPS N.V., Eindhoven (NL)

(72) Inventors: Grzegorz Andrzej Toporek, Boston, MA (US); Sean Joseph Kyne, Brookline, MA (US); Marcin Arkadiusz Balicki, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 748 days.

(21) Appl. No.: 16/972,973

(22) PCT Filed: Jun. 19, 2019

(86) PCT No.: PCT/EP2019/066131
§ 371 (c)(1),
(2) Date: Dec. 7, 2020

(87) PCT Pub. No.: WO2020/002067
PCT Pub. Date: Jan. 2, 2020

(65) Prior Publication Data
US 2021/0251715 A1    Aug. 19, 2021

Related U.S. Application Data

(60) Provisional application No. 62/689,920, filed on Jun. 26, 2018.

(51) Int. Cl.
*A61B 90/11* (2016.01)
(52) U.S. Cl.
CPC .................................. *A61B 90/11* (2016.02)

(58) Field of Classification Search
CPC . A61B 90/11; A61B 2017/3405; A61B 34/10; A61B 2034/108; A61B 90/10
See application file for complete search history.

(56) References Cited

U.S. PATENT DOCUMENTS 8,603,180 B2    12/2013    White et al.
2002/0198518 A1    12/2002    Mijus et al.
(Continued)

FOREIGN PATENT DOCUMENTS

CN    206473383 U    9/2017
WO    2016007717 A1    1/2016

OTHER PUBLICATIONS

Morimoto et al: "Design of Patient-Specific Concentric Tube Robots Using Path Planning From 3-D Ultrasound"; IEEE, 2017, pp. 165-168.

(Continued)

*Primary Examiner* — Ashley L Fishback
*Assistant Examiner* — Chima U Igboko

(57) ABSTRACT

A plan-specific instrument template system employing an intervention guide base (20), and an instrument guide design controller (60) for controlling a designing of a plan-specific instrument template (40) including one or more instrument guides for guiding one or more intervention instruments during an percutaneous intervention. In operation, the controller (60) generates and positions a generic instrument template (30) relative to an image segmentation of the intervention guide base (20), the generic instrument template (30) being a geometric representation of the plan-specific instrument template (40) including the/each instrument guide of the generic instrument template (30) having a generic location and a generic orientation of a generic configuration relative to a platform of the generic instrument template (30). In accordance with a treatment plan associated with the percutaneous intervention, the controller (60)

(Continued)

further controls a relocation, a reorientation and/or a reconfiguration of the/each instrument guide of the generic instrument template (30) relative to the platform of the generic instrument template (30).

15 Claims, 10 Drawing Sheets

(56) References Cited

U.S. PATENT DOCUMENTS

| | | | |
|---|---|---|---|
| 2009/0254093 A1 | 10/2009 | White et al. | |
| 2009/0263764 A1* | 10/2009 | Berckmans, III | A61B 34/10 |
| | | | 433/215 |
| 2013/0027477 A1 | 10/2013 | Mercier et al. | |
| 2017/0020623 A1* | 1/2017 | Glossop | A61B 90/11 |

OTHER PUBLICATIONS

PCT/EP2019/066131 ISR & WO, Sep. 23, 2019, 14 Page Document.

* cited by examiner

PLAN-SPECIFIC INSTRUMENT TEMPLATE FOR PERCUTANEOUS INTERVENTIONAL PROCEDURES

CROSS-REFERENCE TO PRIOR APPLICATIONS

This application is the U.S. National Phase application under 35 U.S.C. § 371 of International Application No. PCT/EP2019/066131, filed on Jun. 19, 2019, which claims the benefit of U.S. Provisional Patent Application No. 62/689,920, filed on Jun. 26, 2018. These applications are hereby incorporated by reference herein.

FIELD OF THE INVENTION

The present disclosure generally relates to an accurate positioning of instruments during a percutaneous interventional procedure via an instrument guide. The present disclosure specifically relates to a formation and generation of a plan-specific instrument template for a percutaneous interventional procedure.

BACKGROUND OF THE INVENTION

Percutaneous interventional procedures involve a positioning of a plurality of elongated instruments (e.g., needles or electrodes) within a patient according to a treatment plan. Examples of such percutaneous interventional procedures include, but are not limited to, transperineal prostate brachytherapy or biopsy, lumbar spine radiofrequency or microwave ablation, facet joint injections and irreversible electroporation with multiple electrodes.

Most of the percutaneous interventional procedures are very challenging because such elongated instruments need to be positioned at a certain accuracy according to the treatment plan. More particularly, the main challenges of percutaneous interventional procedures are related to long procedures times, overuse of both contrast media and imaging radiation (e.g., X-ray) and difficulty in integrating and reproducing very complex multiple-instrument treatment plans into the intraoperative clinical situation.

One solution for an accurate positioning of elongated instruments according to a treatment plan during a percutaneous interventional procedure is the use of a stereotactic interventional navigations systems. Generally, availability of a preoperative treatment plan and its registration with current surgical site is a great advantage of stereotactic interventional navigation systems, and several clinical sites have successfully introduced stereotactic interventional navigation systems for complex multiple needle procedures into their every-day practice. However, these stereotactic interventional navigation systems are usually cumbersome to use and may require remarkable changes into existing clinical workflows, especially because of their strong dependency on general anesthesia. More particularly, stereotactic interventional navigation systems for multiple-instrument percutaneous needle interventions may be difficult to setup and integrate into existing clinical workflows, especially when usage of general anesthesia is imposed, and may be costly because of expensive tracking technologies incorporated into the systems.

Another solution for an accurate positioning of elongated instruments according to a treatment plan during a percutaneous interventional procedure is the use of a generic rigid templates with multiple through guiding holes. Generally, generic rigid templates have been successfully deployed in percutaneous interventional procedures, such as, for example, transperineal prostate interventions including brachytherapy, biopsy, and electroporation. While generic rigid templates are considered to be less expensive than stereotactic interventional navigation systems but sufficiently robust for percutaneous interventional procedures, there are several main limitations of generic rigid needle templates for percutaneous interventional procedures. One such limitations is a large and bulky design of rigid templates due to their generic nature (rigid templates need to cover relatively large surgical access areas and provide enough flexibility in selection of needle entry points). Another limitation is a specificity of a generic rigid template to particular application(s) (e.g., generic rigid templates specifically designed for transperineal prostate interventions) whereby such templates have guide holes of a certain diameter, non-configurable needle orientation angles, and even but non-configurable spacing between holes. The result is non-configurable spacing in the template may enforce undesirable needle entry points. Yet another limitation is an inflexibility of generic rigid templates in terms of workflow because generic rigid templates need to be deployed before the image acquisition and planning of instrument trajectories is constrained by the evenly spaced through guide holes on the generic rigid template.

SUMMARY OF THE INVENTION

The inventions of the present disclosure address the challenges of stereotactic interventional navigations systems and generic rigid templates by providing a plan-specific instrument template for percutaneous interventions involving a plurality of elongated intervention instrument (e.g., needles or electrodes). A plan-specific instrument template of the present disclosure is designed from a preoperative or an intraoperative imaging of a guide base fixed relative to a patient for supporting a development of a treatment plan for the patient, and may be preoperatively or intraoperatively generated using an additive manufacturing process or a subtractive manufacturing process.

One embodiment of the inventions of the present disclosure is a plan-specific instrument template system employing an intervention guide base, and an instrument guide design controller for controlling a designing of a plan-specific instrument template including a platform and one or more instrument guides extending through the platform for guiding one or more intervention instruments during an percutaneous intervention.

In operation, the controller generates and positions a generic instrument template relative to an image segmentation of the intervention guide base, the generic instrument template being a geometric representation of the plan-specific instrument template including reconfiguration of the one tube guide or each instrument guide of the generic instrument template having a generic location and a generic orientation of a generic configuration relative to the platform of the generic instrument template.

In accordance with a treatment plan associated with the percutaneous intervention, the controller further controls a relocation, a reorientation and/or a reconfiguration of the one tube guide or each instrument guide of the generic instrument template relative to the guide surface of the generic instrument template.

A second embodiment of the inventions of the present disclosure is a instrument guide design controller for controlling a designing of a plan-specific instrument template including a platform and one or more instrument guides extending through the platform for guiding one or more intervention instruments during an percutaneous intervention.

The instrument guide design controller employs a generic instrument template generator configured to generate and position the generic instrument template relative to the image segmentation of the intervention guide base, the generic instrument template being a geometric representation of the plan-specific instrument template including reconfiguration of the one tube guide or each instrument guide of the generic instrument template having a generic location and a generic orientation of a generic configuration relative to the platform of the generic instrument template.

The instrument guide design controller further employs a plan-specific instrument template designer configured to control the relocation, the reorientation and/or the reconfiguration of the one tube guide or each instrument guide of the generic instrument template relative to the platform of the generic instrument template in accordance with the treatment plan associated with the percutaneous intervention.

A third embodiment of the inventions of the present disclosure is an instrument guide design method for designing a plan-specific instrument template including a platform and one or more instrument guides extending through the platform for guiding one or more intervention instruments during an percutaneous intervention.

The instrument guide design method involves the instrument guide design controller generating and positioning the generic instrument template relative to the image segmentation of the intervention guide base, the generic instrument template being a geometric representation of the plan-specific instrument template including reconfiguration of the one tube guide or each instrument guide of the generic instrument template having a generic location and a generic orientation of a generic configuration relative to the platform of the generic instrument template.

The instrument guide design method further involves the instrument guide design controller controlling the relocation, the reorientation and/or the reconfiguration of the one tube guide or each instrument guide of the generic instrument template relative to the platform of the generic instrument template in accordance with a treatment plan associated with the percutaneous intervention.

For purposes of describing and claiming the inventions of the present disclosure:
(1) terms of the art including, but not limited to, "percutaneous intervention", "intervention instrument", "image segmentation", "computer mesh" and "elastic deformation", are to be interpreted as known in the art of the present disclosure and as exemplary described in the present disclosure;
(2) Examples of intervention instruments suitable for the treatment planning include but are not limited to, radiofrequency instruments, microwave or electroporation electrodes, facet joint injection needles, biopsy needles, local ablation applicators, endoscopes, intraoperative imaging modalities (e.g., ultrasound transducers), treatment applicators and pedicle screws;
(3) the term "instrument guide" broadly encompasses any and all structures as known in the art of the present disclosure and hereinafter conceived, utilized for guiding intervention instruments to target locations in an anatomical object.
(4) the term "instrument guide base" broadly encompasses all structures, known in the art of the present disclosure and hereinafter conceived, that are mountable to a patient body for supporting an instrument guide in accordance with the inventive principles of the present disclosure;
(5) the term "generic instrument template" broadly encompasses any and all geometric representations of an instrument guide, as known in the art of the present disclosure and hereinafter conceived, that are generically configured for percutaneous interventions in accordance with the inventive principles of the present disclosure;
(6) the term "plan-specific instrument template" broadly encompasses any and all instrument guides, known in the art of the present disclosure and hereinafter conceived, that are manufactured from a configuration of a generic instrument template in accordance with a treatment plan of a particular percutaneous intervention in accordance with the inventive principles of the present disclosure;
(7) the term "instrument guide" broadly encompasses any and all structures, known in the art of the present disclosure and hereinafter conceived, forming a passage for intervention instruments. Examples of instrument guides include, but are not limited to, needle guides, acoustic window guides for ultrasound probes and guide holes with or without a specific orientation;
(8) the term "percutaneous intervention system" broadly encompasses any and all percutaneous intervention systems as known in the art of the present disclosure and hereinafter conceived, and the term "plan-specific instrument template system" broadly encompasses a percutaneous intervention system incorporating the inventive principles of the present disclosure;
(9) the term "percutaneous intervention method" broadly encompasses any and all percutaneous intervention methods as known in the art of the present disclosure and hereinafter conceived, and the term "plan-specific instrument template method" broadly encompasses a percutaneous intervention method incorporating the inventive principles of the present disclosure;
(10) the term "controller" broadly encompasses all structural configurations, as understood in the art of the present disclosure and as exemplary described in the present disclosure, of an application specific main board or an application specific integrated circuit for controlling an application of various inventive principles of the present disclosure as exemplary described in the present disclosure. The structural configuration of the controller may include, but is not limited to, processor(s), computer-usable/computer readable storage medium(s), an operating system, application module(s), peripheral device controller(s), slot(s) and port (s);
(11) the term "application module" broadly encompasses an application incorporated within or accessible by a controller consisting of an electronic circuit (e.g., electronic components and/or hardware) and/or an executable program (e.g., executable software stored on non-transitory computer readable medium(s) and/or firmware) for executing a specific application;
(12) the descriptive labels for application modules described and claimed herein facilitate a distinction between application modules as described and claimed herein without specifying or implying any additional limitation to the term "controller";
(12) the term "data" broadly encompasses all forms of a detectable physical quantity or impulse (e.g., voltage, current, or magnetic field strength) as understood in the art of the present disclosure and as exemplary described in the present disclosure for transmitting information and/or instructions in support of applying various inventive principles of the present disclosure as subsequently described in the present disclosure. Data communication various components of the present disclosure may involve any communication method as known in the art of the present disclosure including, but not limited to, data transmission/reception over any type of wired or wireless datalink and a reading of data uploaded to a computer-usable/computer readable storage medium; and

(14) the descriptive labels for data as described and claimed herein facilitate a distinction between data as described and claimed herein without specifying or implying any additional limitation to the term "data".

The foregoing embodiments and other embodiments of the inventions of the present disclosure as well as various structures and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of the present disclosure being defined by the appended claims and equivalents thereof.

DETAILED DESCRIPTION OF THE PREFERRED EMBODIMENTS

Figure 1A:
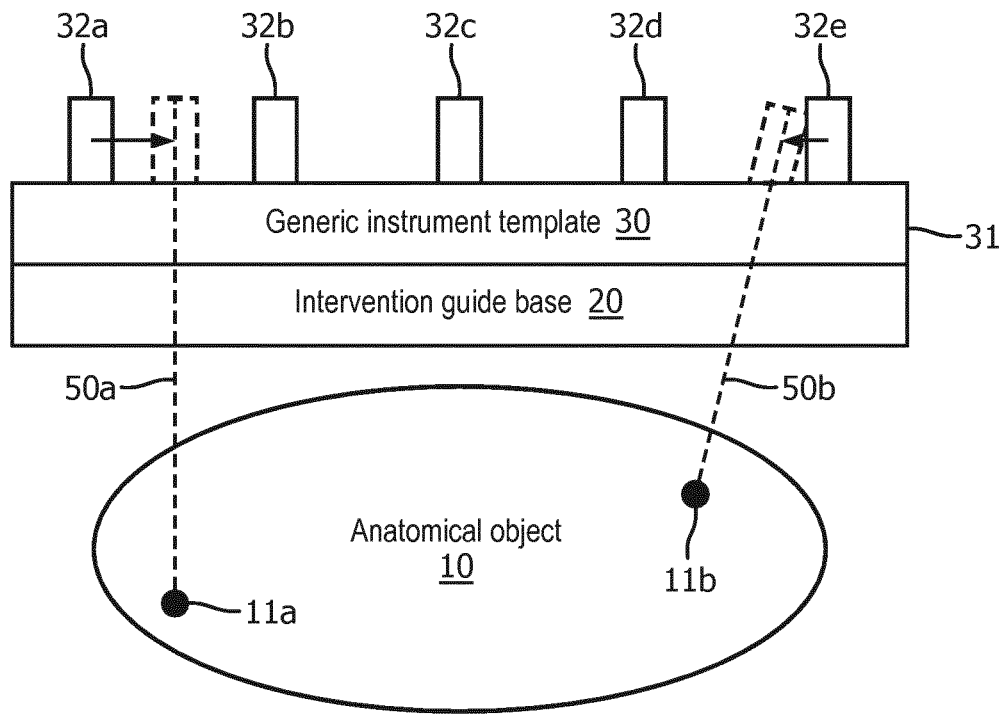
FIG. 1A illustrates an exemplary embodiment of a planning phase of a percutaneous intervention involving a generic instrument template and an intervention guide base in accordance with the inventive principles of the present disclosure.
Figure 1B:
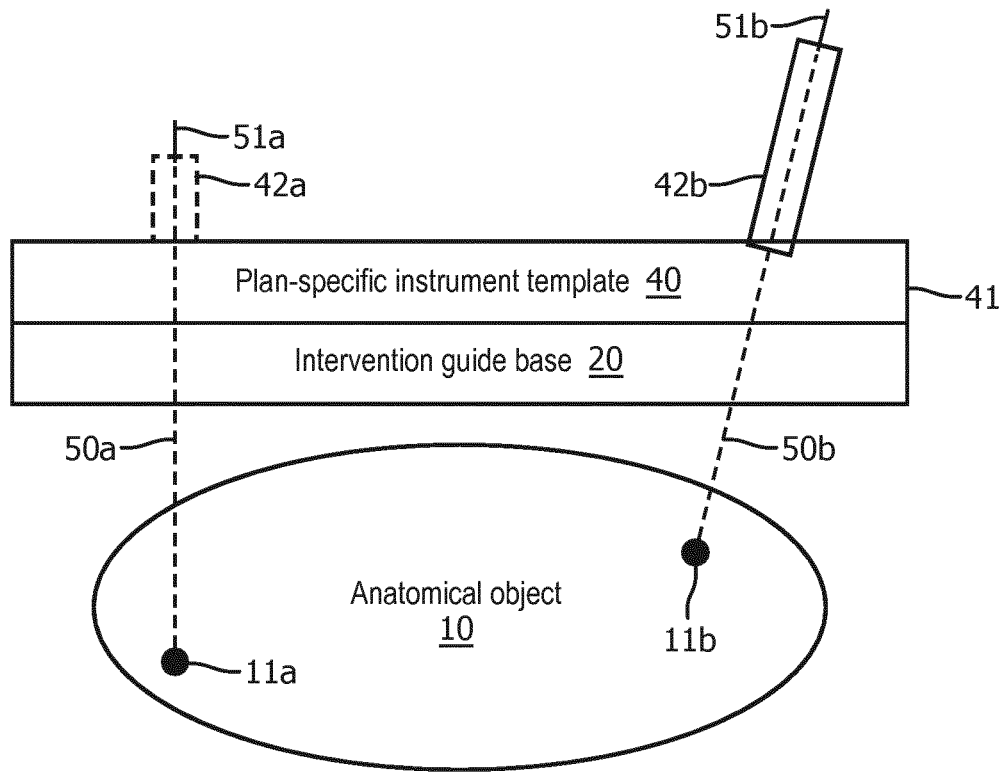
FIG. 1B illustrates an exemplary embodiment of an intervention phase of a percutaneous intervention involving a plan-specific instrument template and an intervention guide base in accordance with the inventive principles of the present disclosure.

To facilitate an understanding of the various inventions of the present disclosure, the following description of FIGS. 1A and 1B teaches basic inventive principles of a planning phase and an intervention phase of a percutaneous intervention in accordance with the present disclosure. From this description, those having ordinary skill in the art will appreciate how to apply the inventive principles of the present disclosure of additional embodiments of a percutaneous intervention in accordance with the inventive principles of the present disclosure.

Referring to FIG. 1A, a planning phase of a percutaneous intervention in accordance with the present disclosure involves an imaging of an intervention guide base 20 relative to an anatomical object 10 that is the subject of the percutaneous intervention. In practice, the imaging may be executed by an imaging modality as known in the art of the present disclosure (e.g., computed-tomography ("CT"), cone-beam CT, magnetic resonance imaging, ultrasound, positron emission tomography and single-photon emission computed tomography).

Subsequent to the imaging of an intervention guide base 20 relative to an anatomical object 10, the intervention guide base 20 is image segmented whereby a generic instrument template 30 is generated in the form of a computer mesh positioned onto the segmented intervention guide base 20. Generic instrument template 30 includes a platform 31 positionable onto segmented intervention guide base 20. Generic instrument template 30 further includes instrument guides 32 extending through platform with each instrument guide 32 having a generic location, a generic orientation and a generic configuration (i.e., shape and dimensions) relative to platform 31. More particularly, the location, the orientation and the configuration of each instrument guide 32 are unrelated to the subject percutaneous intervention.

Subsequent to the generating and the positioning of generic instrument template 30, an treatment plan is developed to delineate within the image of an instrument trajectory of one or more intervention instruments (e.g., needle(s) and/or electrode(s)) sequentially through generic instrument template 30 and intervention guide base 20 to a target location within anatomical object 10. For example, as shown in FIG. 1A, two (2) instrument trajectory 50 are delineated through generic instrument template 30 and intervention guide base 20 to two (2) respective target locations 11a and 11b within anatomical object 10.

For each delineated instrument trajectory 50, the present disclosure provides for a relocation and/or a reorientation of an instrument guide 32 relative to platform 31 to correspond to the delineated instrument trajectory. For example, as shown in FIG. 1A, instrument guide 32a may be laterally shifted to a location corresponding to delineated instrument trajectory 50*a*, and instrument guide 32*e* may be laterally shifted to a location and tilted to an orientation corresponding to delineated instrument trajectory 50*b*.

Also, for each delineated instrument trajectory 50, the present disclosure provides for a reconfiguration of a shape and/or dimensions of an instrument guide 32 relative to platform 31 to correspond to the delineated instrument trajectory. For example, a length and a diameter of a particular one of instrument guides 32 may be adjusted to account for a length and diameter of a particular intervention instrument through that particular one of the instrument guides 32 along the corresponding delineated instrument trajectory and to thereby guide the user not only in terms of a location and an orientation of the trajectory but also in terms of insertion depth. For example, for a shallow target location, an instrument guide may be lengthened and/or narrowed thus limiting the depth of the intervention instrument into the anatomical space, and for a deeper target location, an instrument guide may be shortened and/or widened thus increasing the depth of the intervention instrument into the anatomical space. Alternatively, an intervention instrument may be marked for depth insertion.

The present disclosure further provides for a manufacturing of a plan-specific instrument template based on each relocation, each reorientation and/or each reconfiguration of an instrument guide 32 relative to platform 31 to correspond to a delineated instrument trajectory 50, and a removal of any unused instrument guide 32 from platform 31. For example, as shown in FIG. 1B, a manufactured plan-specific instrument template 40 includes an instrument guide 42*a* located and oriented relative to a platform 41 in accordance with the relocation of instrument guide 32*a* relative to platform 31, and further includes an instrument guide 42*b* located and oriented relative to platform 41 in accordance with the relocation, the reorientation and the reconfiguration of instrument guide 32*e* relative to platform 31 as well as a lengthening of instrument guide 32*c*.

Referring to FIG. 1B, an intervention phase of the percutaneous intervention in accordance with the present disclosure involves a positioning of plan-specific instrument template 40 onto intervention guide base 20, which is positioned relative to anatomical object 10 as in the planning phase of the percutaneous intervention. Subsequent to the positioning of plan-specific instrument template 40 onto intervention guide base 20, an intervention instrument 51*a* may be inserted sequentially through instrument guide 42*a* and intervention guide base 20 to target location 11*a* within anatomical object 10 and an intervention instrument 51*b* may be inserted sequentially through instrument guide 42*b* and intervention guide base 20 to target location 11*b* within anatomical object 10. In practice, such insertion of intervention instruments 51 may be monitored via an imaging of intervention instruments 41 as known in the art of the present disclosure (e.g., computed-tomography ("CT"), cone-beam CT, magnetic resonance imaging, ultrasound, positron emission tomography or single-photon emission computed tomography) and/or a tracking of intervention instruments 41 as known in the art of the present disclosure (e.g., electromagnetic tracking, optical tracking, optical shape sensing or marker-based tracking). Also in practice, as previously described, each instrument guide may be lengthened or shortened in the planning phase to thereby regulate an insertion depth of a corresponding intervention instrument.

Referring to FIGS. 1A and 1B, in practice, intervention guide base 20 may have a material composition and a geometric configuration suitable for one or more particular types of percutaneous interventions. Also in practice, intervention guide base 20 may be attached to, mounted onto or otherwise affixed to a patient body during the planning phase and the intervention phase of a percutaneous intervention of the present disclosure.

Figure 2A:
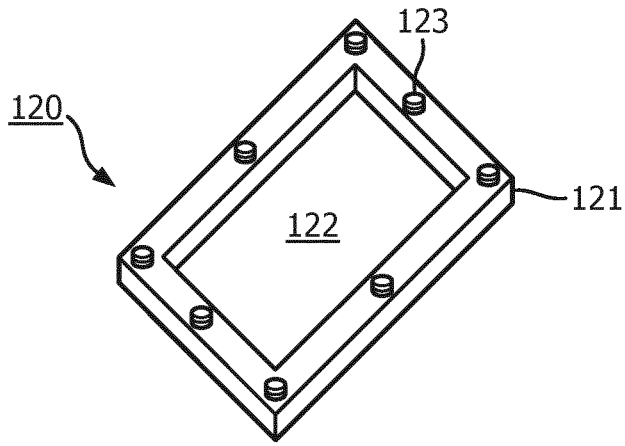
FIG. 2A illustrates an exemplary embodiment of an intervention guide base in accordance with the inventive principles of the present disclosure.

In one embodiment as shown in FIG. 2A, an intervention guide base 120 employs a frame 121 having an instrument passage 122 with frame 121 further having a degree of flexibility to comply with a shape of the patient body. Frame 121 contains a set of uniquely spaced attachment pins 123 located on the top surface to enable easier assembly of intervention guide base to plan-specific instrument template 40. A lower surface of frame 121 contains a self-adhesive tape (not shown), such as, for example hypoallergenic tapes used in urology or under electrocardiography electrodes as known in the art of the present disclosure. Optionally, to enable accurate segmentation of intervention guide base 20 within volumetric images, frame 121 may incorporate a set of internal radiopaque markers or other material distinguishable from human tissue attenuation coefficient.

Furthermore, a self-adhesive base may be reinforced with an attachment belt that surrounds patient body as known in the art of the present disclosure. Such a belt may also allow for dynamic placement of multiple instrument guide bases for different parts of the procedure, and may also allow to quickly clip on and off different instrument guide bases in case of occurrence of intraoperative changes.

Referring to FIG. 1A, in practice, generic instrument template 30 is a computer mesh geometrically representative of a plan-specific instrument template for one or more particular types of percutaneous interventions.

Figure 2B:
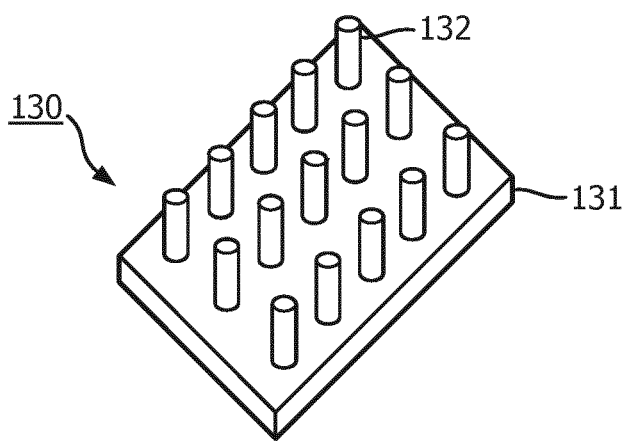
FIG. 2B illustrates an exemplary embodiment of a generic instrument template in accordance with the inventive principles of the present disclosure.

In one embodiment as shown in FIG. 2B, a generic instrument template 130 includes a platform 131 in the form of a generic 3D triangular mesh with a set of generic located and orientated, evenly spaced models of instrument guides 132 on platform 131. This generic mesh is a geometric representation of a plan-specific instrument template 140 (FIG. 2C) that is deformable based in information from both volumetric images and an treatment plan as previously described in the present disclosure.

Further, a lower surface of platform 131 contains a set of holes (not shown) that matches unique configuration defined by pins located on the upper surface of instrument guide base 120 (FIG. 2A). Other possible attachment mechanisms, such as self-adhesive tape, are also possible.

Referring to FIG. 1B, in practice, a deformed generic instrument template 30 is inputted an additive manufacturing system (e.g., a 3D printer) or a subtractive manufacturing system to thereby manufacture plan-specific instrument template 40.

Figure 2C:
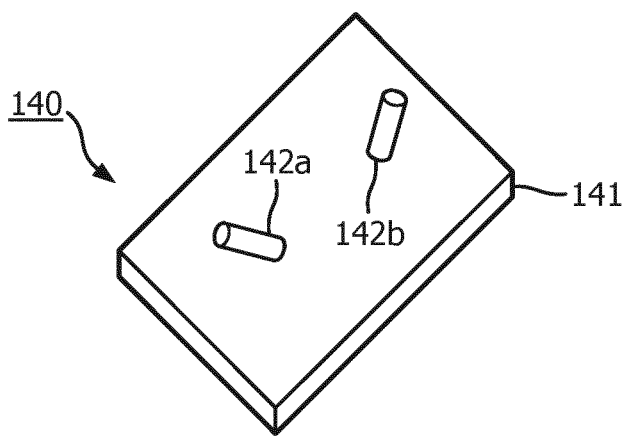
FIG. 2C illustrates an exemplary embodiment of a plan-specific instrument template base in accordance with the inventive principles of the present disclosure.

In one embodiment as shown in FIGS. 2B and 2C, a deformed generic instrument template 130 is stored in a file format usable by additive manufacturing systems or subtractive manufacturing systems (e.g., STL file format, OBJ file format or. VRML file format) whereby the file format serves to manufacture plan-specific instrument template 140.

While instrument guides 142 are shown having tubular segments extending from platform 141, in practice instrument guides may totally be integrated into platform 141 without any extending tubular segments.

Furthermore in practice, instrument guides 142 may be made from a flexible material, whereby a user may adjust a location, an orientation and/or a configuration of instrument guides 142 as needed. Also, instrument guides 142 may be a combination of both rigid material and flexible material whereby a user may slightly adjust a location, an orientation and/or a configuration of instrument guides 142 if needed within a specific range.

Also in practice, a multi-material instrument guide 142 may be manufactured to gauge depth of the insertion of intervention instrument relative to the target location. For example, with a semi-flexible instrument guide 142, the material may compress to indicate a proximity to the target location. Additionally, instrument guides 142 may also be printed with fixed motion ball joints to regulate motion in one or more planes (e.g., only allowing for 'x' degree motion in certain planes).

Referring to FIG. 1B, plan-specific instrument template 40 typically will be preoperatively designed and manufactured during the planning phase. Nonetheless in practice, plan-specific instrument template 40 may be preoperatively designed during the planning phase and intraoperatively manufactured during the intervention phase. Issues associated with an intraoperative manufacture of the plan-specific instrument template 40 the intervention phase include (1) speed of manufacturing, (2) bio-compatibility and (3) post-production disinfection.

For example, a high speed additive manufacturing process or a high speed subtractive manufacturing process as known in the art of the present disclosure may be used to comply with a time-constraint of the percutaneous intervention (e.g., several minutes). Further, while plan-specific instrument template 40 will typically have limited contact with the patient body and very short exposure time, plan-specific instrument template 40 should have a material composition according to medial regulatory standards (e.g., PolyJet photopolymer MED610). Finally, intervention guide base 20 may be disinfected before the percutaneous intervention during the manufacturing process plan-specific instrument template 40 using steam autoclaves or plazma sterilization or with ethyl alcohol (70%) as disinfectant.

To further understand the embodiments of FIGS. 2A-2C, FIGS. 3A-3C illustrate an exemplary percutaneous intervention of a spine 111 of a patient incorporating an intervention guide base 120, generic instrument template 130 and plan-specific instrument template 140.

Figure 3A:
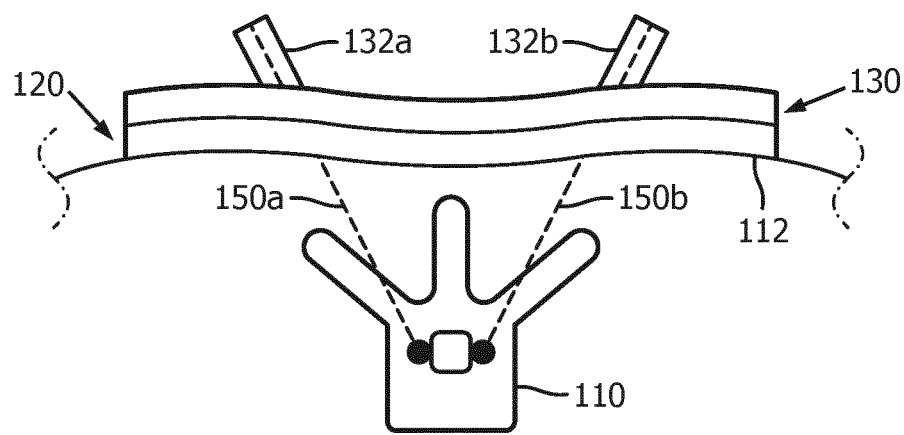
FIG. 3A illustrates an exemplary design of the plan-specific instrument template of FIG. 2C in accordance with the inventive principles of the present disclosure.

FIG. 3A illustrates an image segmented intervention guide base 120 flexibly and adhesively attached to a patient body 112 whereby an treatment plan of two (2) instrument path 150*a* to target locations within spine 111 to thereby facilitate a deforming of instrument guides 132 of generic instrument template 130 in accordance with the treatment plan.

Figure 3B:
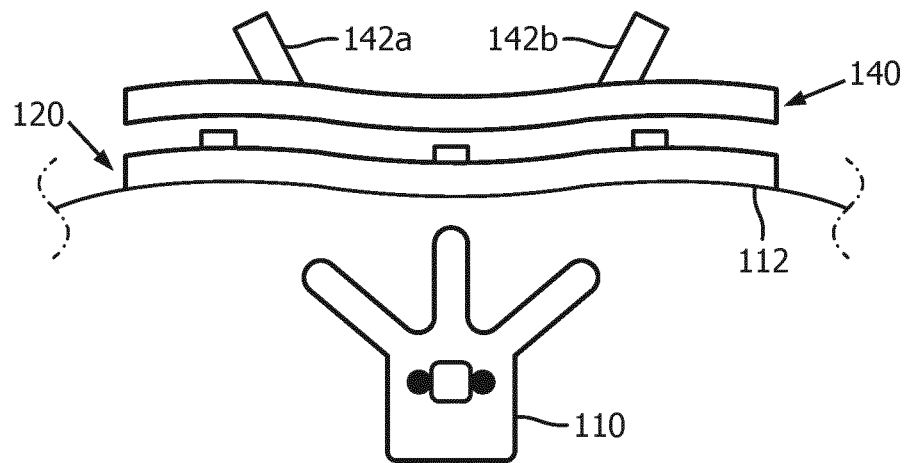
FIG. 3B illustrates an exemplary manufacturer of the plan-specific instrument template of FIG. 2C in accordance with the inventive principles of the present disclosure.

FIG. 3B illustrates a manufacture of plan-specific intervention template 140 prior to an attachment of plan-specific intervention template 140 to intervention guide base 120.

Figure 3C:
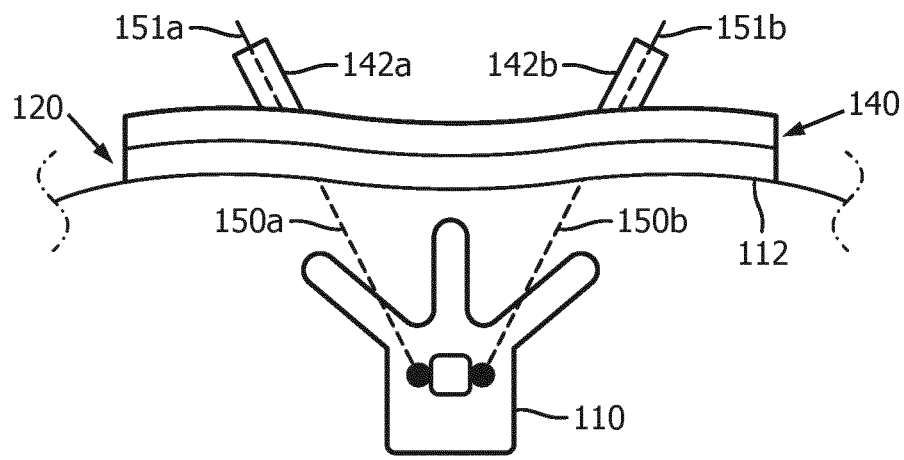
FIG. 3C illustrates an exemplary intervention involving the plan-specific instrument template of FIG. 2C in accordance with the inventive principles of the present disclosure.

FIG. 3C illustrates a mounting of plan-specific intervention guider 140 onto intervention guide base 120 whereby intervention instruments 151 may be accurately guided to the target locations in spine 111.

Figure 4:
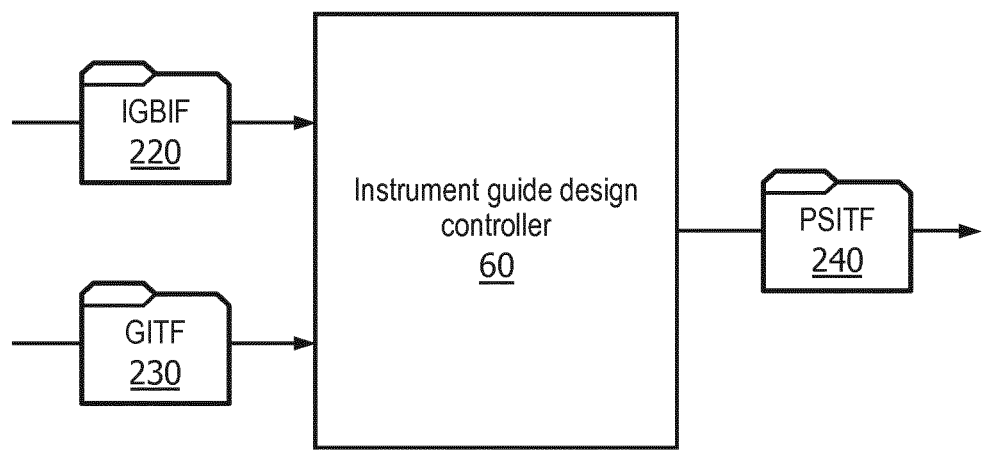
FIG. 4 illustrates an exemplary instrument guide design controller in accordance with the inventive principles of the present disclosure.
Figure 5:
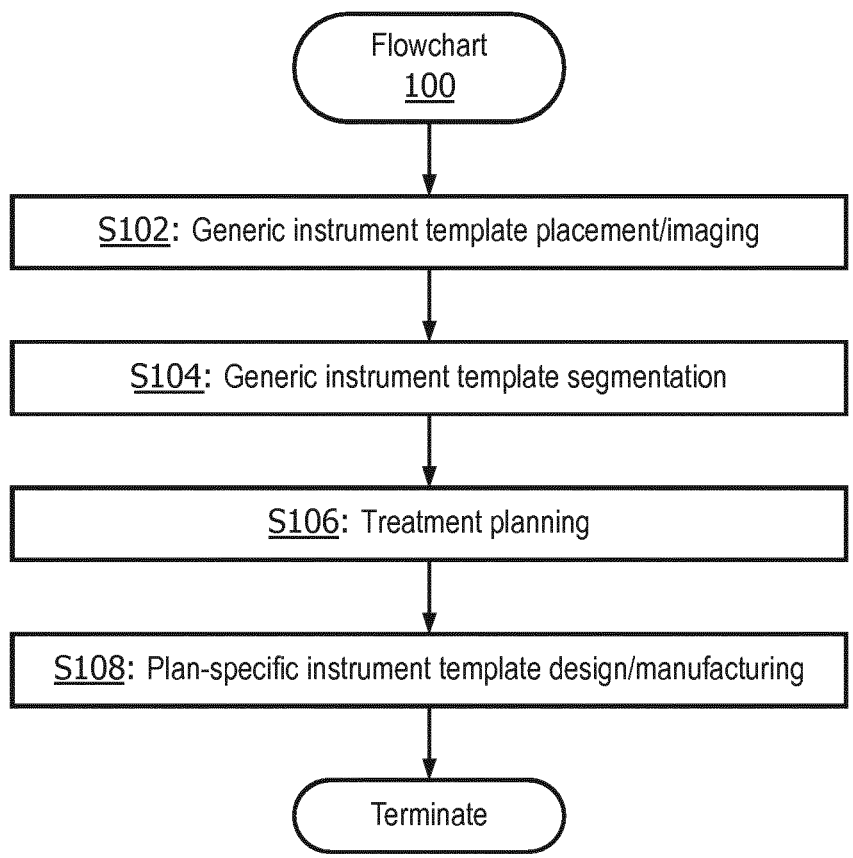
FIG. 5 illustrates an exemplary flowchart of an instrument guide design method in accordance with the inventive principles of the present disclosure.

To facilitate a further understanding of the various inventions of the present disclosure, the following description of FIGS. 4 and 5 teaches basic inventive principles of an instrument guide design controller of the present disclosure and an instrument guide design method of the present disclosure. From this description, those having ordinary skill in the art will appreciate how to apply the inventive principles of the present disclosure for making and using additional embodiments of instrument guide design controllers of the present disclosure and instrument guide design controller of the present disclosure.

Referring to FIG. 4, an instrument guide design controller 60 of the present disclosure inputs an intervention guide base image file 220 including data of an imaging of an intervention guide base of the present disclosure (e.g., intervention guide base 120 shown in FIG. 2A) relative to an anatomical object that is a subject of a percutaneous intervention, and further inputs (or alternatively stores) a generic instrument template file 230 including data for a generation of a generic instrument template of the present disclosure (e.g., generic instrument template 130 shown in FIG. 2B). From the inputs, instrument guide design controller 60 outputs a plan-specific instrument template file 240 including data for an additive manufacturing or a subtractive manufacturing of a plan-specific instrument template of the present disclosure (e.g., plan-specific instrument template 140 shown in FIG. 2C).

Generally, instrument guide design controller 60 is configured to (a) segment an intervention guide base of the present disclosure from pre-operative volumetric images or intra-operative volumetric images, (b) define, via a generic instrument template of the present disclosure, an treatment plan that contains a plurality of instrument trajectories/paths, and (c) design of a plan-specific instrument template of the present disclosure.

During the segmentation process, instrument guide design controller 60 automatically segments an intervention guide base of the present disclosure from the volumetric images using one of the methods known in art of the present disclosure (e.g., thresholding, level set, or active contours segmentation algorithms), or via a manual segmentation by delineation of the intervention guide base.

Defining the treatment plan includes interventional instrument trajectories/paths identified by a user of instrument guide design controller 60 via a graphical user interface on the volumetric images (e.g., CT, CBCT, MRI, PET-CT, etc.) Examples of intervention instruments suitable for the treatment planning include but are not limited to, radiofrequency instruments, microwave or electroporation electrodes, facet joint injection needles, biopsy needles, local ablation applicators, endoscopes, intraoperative imaging modalities (e.g., ultrasound transducers), treatment applicators and pedicle screws. An instrument path is defined as a point-to-point needle access path to percutaneously reach the clinical site, and an instrument path consists of a target location and a skin-entry point. Preferably, trajectories are defined manually by the user of instrument guide design controller 60, but other automatic methods that incorporates both the position of the instrument guide base and the anatomical knowledge of the surgical site may be applied as known in the art of the present disclosure.

The design of the plan-specific instrument template is derived from a deformation of the generic instrument template in accordance with the treatment plan as previously described in the present disclosure.

In one embodiment, instrument guide design controller 60 executes a flowchart 100 representative of an instrument guide design method of the present disclosure as shown in FIG. 5. While flowchart 100 will be described in connection with an exemplary percutaneous intervention of a spine of a patient incorporating an intervention guide base 120, generic instrument template 130 and plan-specific instrument template 140 of FIGS. 2A-2C, those having ordinary skill in the art will appreciate how to apply flowchart 100 to any embodiments of an intervention guide base, a generic instrument template and a plan-specific instrument template of the present disclosure.

Referring to FIG. 5, prior to image acquisition, a stage S102 of flowchart 100 involving a physician/clinician attaching a self-adhesive instrument guide base 120a above the surgical site. In practice, the physician/clinician determining a right position of instrument guide base 120a above the surgical site may require previous diagnostic scan(s) or usage of metallic wires previously attached around the surgical site. For this example, the surgical site is a level in the vertebral column in which pedicle screws will be implanted. In one embodiment, instrument guide base 120a is used in the areas of a patient body that are not susceptible to respiratory motion and soft-tissue deformation. Because of any degree of rigidity of instrument guide base 120, respiratory motion could significantly influence the instrument positioning accuracy of plan-specific instrument template 140 due to organ motion. In another embodiment, a coupling or a registering of instrument guide base 120 with real-time imaging modalities may enhance the capabilities of the plan-specific instrument template 140 in dynamic motion of the patient body.

Figure 6A:
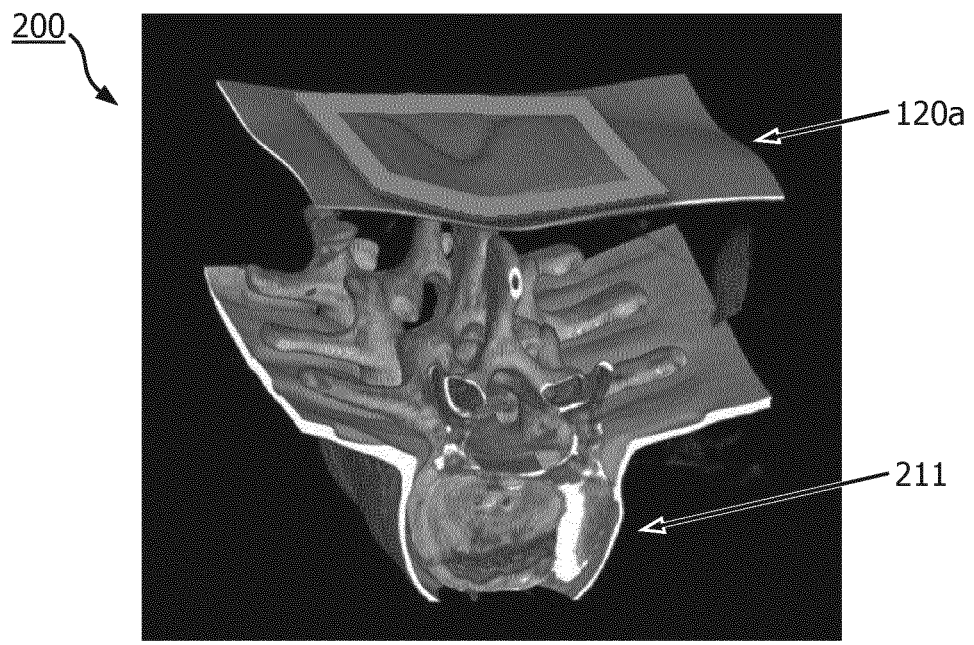
FIGS. 6A, 6B, 6C and 6D illustrate an exemplary execution of the flowchart of FIG. 5.

Upon the placement of instrument guide base 120, a volumetric image dataset is acquired and transferred as file 220 to instrument guide design controller 60 (FIG. 4). FIG. 6A illustrates an exemplary imaging 200 of instrument guide base 120 relative to a spine 111a.

Figure 6B:
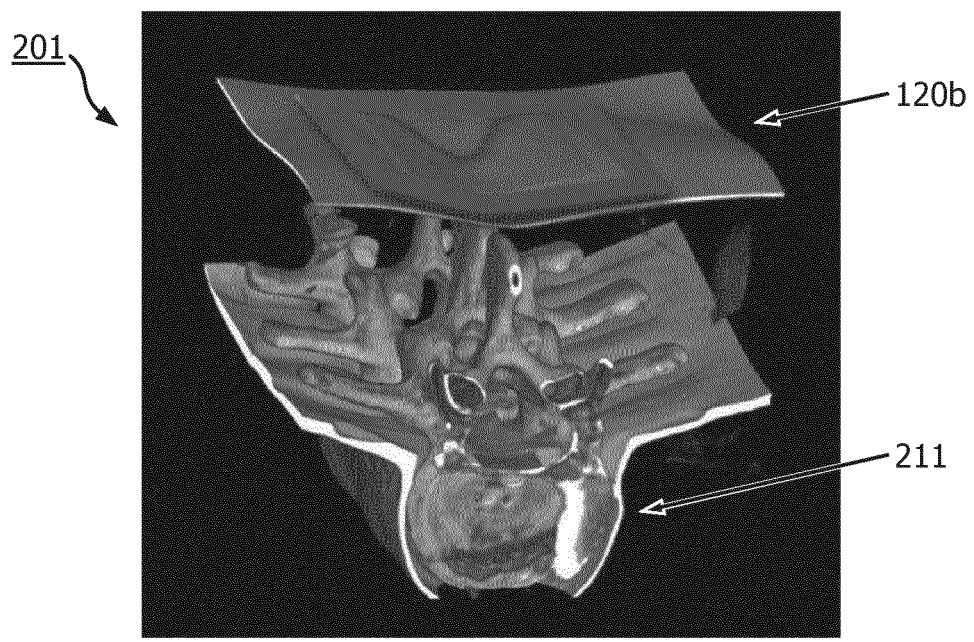
Figure 6C:
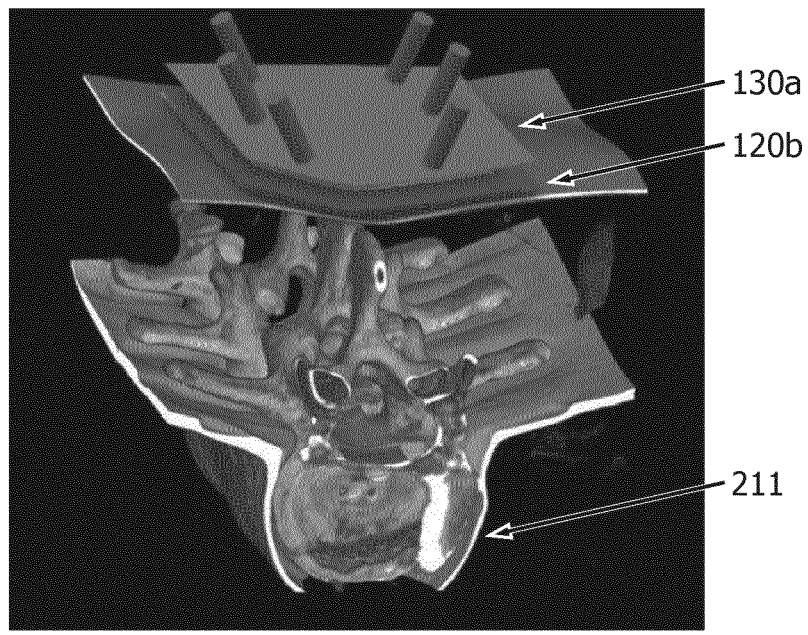

Still referring to FIG. 5, a stage S104 of flowchart 100 encompasses instrument guide design controller 60 generating a model 120b of an instrument guide base 120a via image segmentation as shown in FIG. 6B. More particularly, during the image segmentation, voxels belonging to a specific objects are grouped and labelled using an arbitrary scalar value. Usage of a building material of instrument guide base 120a with unique attenuation coefficient compared to human tissue could simplify the process After segmentation, stage S140 further encompasses instrument guide design controller 60a generating generic instrument template 130 as shown in FIG. 6C using methods known in art of the present disclosure (e.g., Delaunay triangulation). As a post-processing step, generic instrument template 130 may be simplified and cleaned using a decimation method.

Figure 6D:
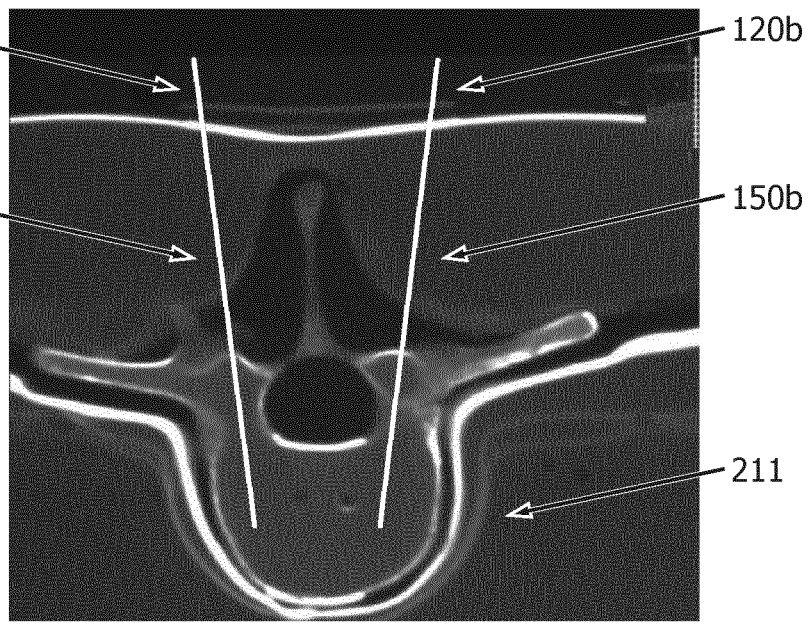

Still referring to FIG. 5, a stage S106 of flowchart 100 encompasses instrument guide design controller 60 facilitating a defined treatment plan containing single or plural instrument trajectories (e.g., instrument trajectories 150 shown in FIG. 6D). In one embodiment, instrument trajectories are defined manually by the physician/clinician. Alternatively, in another embodiment, automatic methods that incorporate both the position of the model 120b of an instrument guide base 120a and the anatomical knowledge of the surgical site may be used by instrument guide design controller 60 to define the instrument trajectories.

Still referring to FIG. 5, a stage S108 of 100 encompasses instrument guide design controller 60 designing 3D model 140a of plan-specific multiple needle template 140 based on the model 120b of an instrument guide base 120a, the generic instrument template 130 and the treatment plan containing desired instrument trajectories.

In one embodiment, generic instrument template 130 is introduced by instrument guide design controller 60 to elastic deformation using one of the deformable models algorithms known in the art of the present disclosure that are successfully applied in non-rigid image registration, finite element analysis and other simulations (e.g., deformable surfaces or level set). During the elastic deformation, internal deformation energy may expand the generic mesh under constrains imposed by upper surface of the model 120b of an instrument guide base 120a and attachment pins. In a simplified version, the upper surface of the model 120b of an instrument guide base 120a will define the lower surface of generic instrument template 130 whereby the lower surface of generic instrument template 130 will be expanded in the direction opposite to the patient body to reach a certain thickness (e.g. 2 mm). Attachment pins on model 120b will generate its counterparts-attachment holes-on the lower surface of generic instrument template 130. Positions of through holes for needles (entry points) are defined as an intersection between instrument trajectory and an upper surface of generic instrument template 130. Diameters of through holes of the instrument guides are defined by the known diameter of the instrument (known a priori from internal database). A length of an instrument guide is defined by subtracting length of a vector defined by target and entry point on the upper surface of generic instrument template 130 from the instrument length (known a priori from internal database). Orientation of the instrument guides are calculated from instrument orientation angles derived from the treatment plan.

Upon termination of flowchart 100, plan-specific instrument template file 240 enables an additive manufacturing or subtractive manufacturing of plan-specific instrument template 140.

Figure 7:
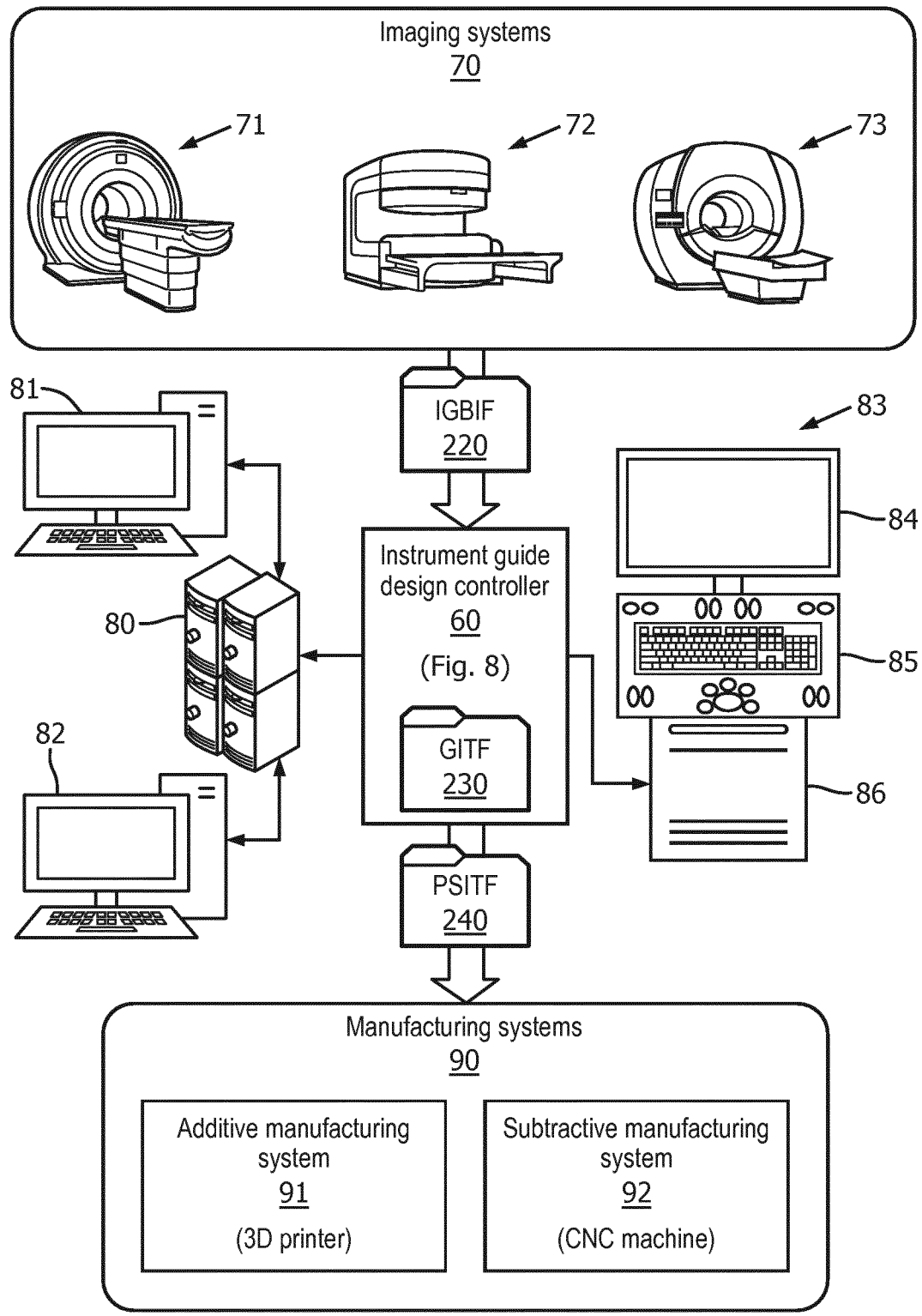
FIG. 7 illustrates an exemplary embodiment of an instrument guide design system in accordance with the inventive principles of the present disclosure.

To facilitate a further understanding of the various inventions of the present disclosure, the following description of FIG. 7 teaches basic inventive principles of an instrument guide design system of the present disclosure. From this description, those having ordinary skill in the art will appreciate how to apply the inventive principles of the present disclosure for making and using additional embodiments of instrument guide design systems of the present disclosure.

Figure 8:
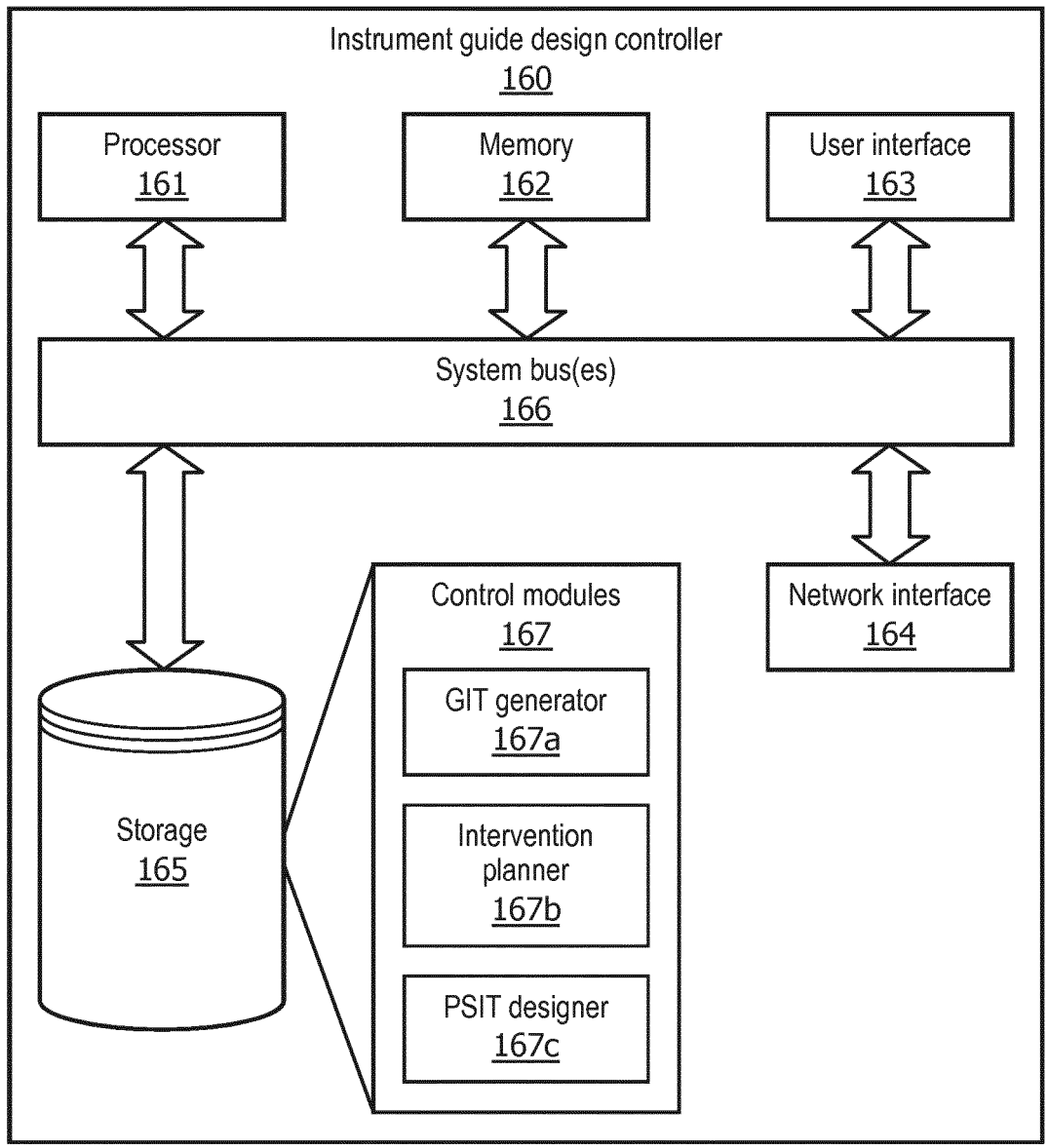
FIG. 8 illustrates an exemplary embodiment of an instrument guide design controller in accordance with the inventive principles of the present disclosure.

Referring to FIG. 8, an instrument guide design controller 60 of the present disclosure is installed within an application server 80 accessible by a plurality of clients (e.g., a client 81 and a client 82 as shown) and/or is installed within a workstation 83 employing a monitor 84, a keyboard 85 and a computer 86.

In operation, instrument guide design controller 60 inputs instrument guide base image file 220 (FIG. 4) from one or more imaging systems 70 (e.g., MRI imaging systems 71-73) to output plan-specific instrument template file 240 (FIG. 4), which is communicated by controller 60 to one or more manufacturing sources 90 including, but not limited to, an additive manufacturing systems 91 (e.g., a 3D printer) and a subtractive manufacturing system 92 (e.g., a CNC machine).

In practice, instrument guide design controller 60 may be implemented as hardware/circuitry/software/firmware.

In one embodiment as shown in FIG. 9, an instrument guide design controller 160 includes a processor 161, a memory 162, a user interface 163, a network interface 164, and a storage 165 interconnected via one or more system bus(es) 166. In practice, the actual organization of the components 161-165 of controller 160a may be more complex than illustrated.

The processor 161 may be any hardware device capable of executing instructions stored in memory or storage or otherwise processing data. As such, the processor 161 may include a microprocessor, field programmable gate array (FPGA), application-specific integrated circuit (ASIC), or other similar devices.

The memory 162 may include various memories such as, for example L1, L2, or L3 cache or system memory. As such, the memory 162 may include static random access memory (SRAM), dynamic RAM (DRAM), flash memory, read only memory (ROM), or other similar memory devices.

The user interface 163 may include one or more devices for enabling communication with a user such as an administrator. For example, the user interface 163 may include a display, a mouse, and a keyboard for receiving user commands. In some embodiments, the user interface 163 may include a command line interface or graphical user interface that may be presented to a remote terminal via the network interface 164.

The network interface 164 may include one or more devices for enabling communication with other hardware devices. For example, the network interface 164 may include a network interface card (NIC) configured to communicate according to the Ethernet protocol. Additionally, the network interface 164 may implement a TCP/IP stack for communication according to the TCP/IP protocols. Various alternative or additional hardware or configurations for the network interface will be apparent.

The storage 165 may include one or more machine-readable storage media such as read-only memory (ROM), random-access memory (RAM), magnetic disk storage media, optical storage media, flash-memory devices, or similar storage media. In various embodiments, the storage 165 may store instructions for execution by the processor 161 or data upon with the processor 161 may operate. For example, the storage 165 store a base operating system (not shown) for controlling various basic operations of the hardware.

More particular to the present disclosure, storage 165 further stores control modules 167.

A first control module 167 is a generic instrument template generator 167a for executing an image segmentation of an instrument guide base of the present disclosure and a mesh generation of a generic instrument template of the present disclosure (e.g., stage S104 of flowchart 100 shown in FIG. 5).

A second control module 167 is a treatment planner 167b for executing a delineation of instrument trajectories (e.g., a stage S106 of flowchart 100 shown in FIG. 5).

A third control module 167 is a plan-specific instrument template designer 167c for executing a deformation the mesh generation of the generic instrument template of the present disclosure in accordance with the treatment plan to thereby design a plan-specific instrument template of the present disclosure (e.g., a stage S106 of flowchart 100 shown in FIG. 5).

Referring to FIGS. 1A and 1B, while instrument guide base 20 of the present disclosure is important for the planning phase of a percutaneous intervention of the present disclosure, alternative devices may be substituted for instrument guide base 20 during the intervention phase of the percutaneous intervention of the present disclosure.

Figure 9A:
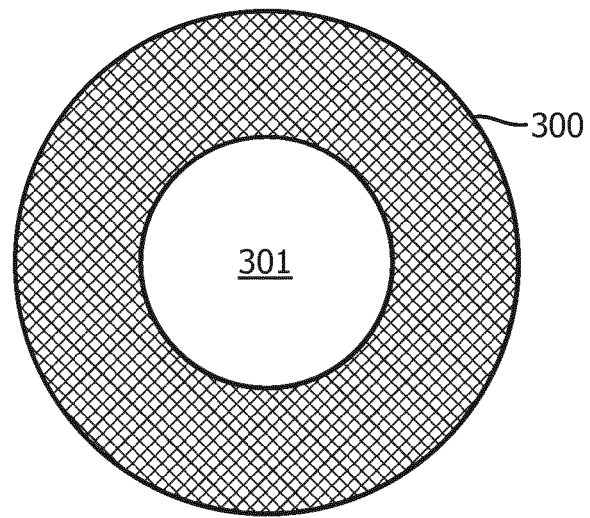
FIG. 9A illustrates an exemplary ultrasound array as known in the art of the present disclosure.
Figure 9B:
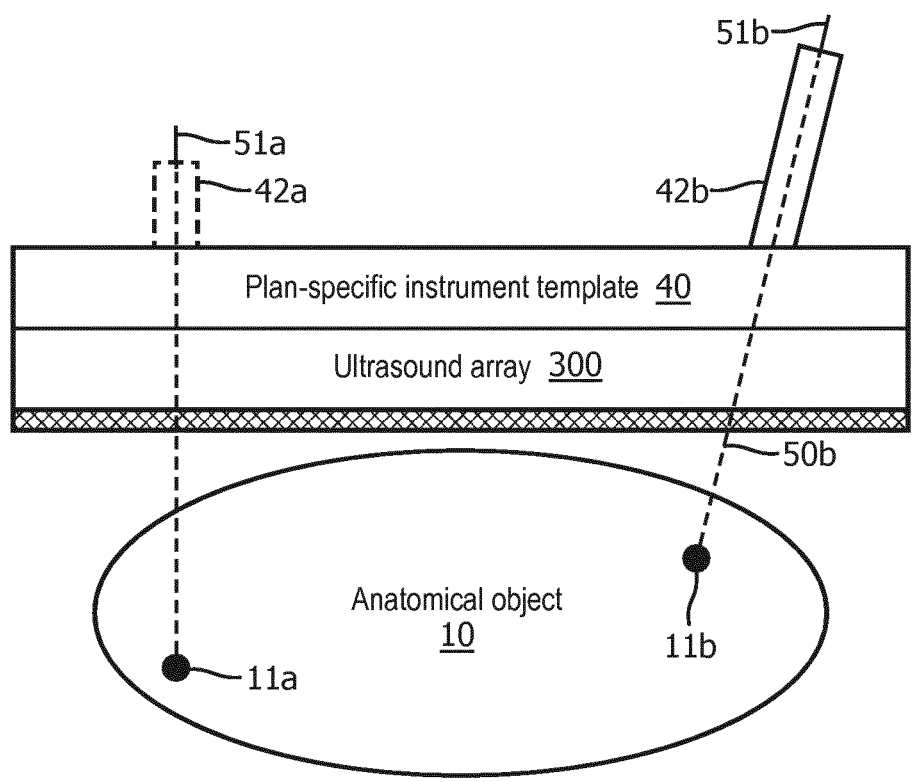
FIG. 9B illustrates an exemplary embodiment of an intervention phase of a percutaneous intervention involving a plan-specific instrument template and the ultrasound array in accordance with the inventive principles of the present disclosure.

For example, FIG. 9A illustrates a bottom view of a large ultrasound array 300 having an instrument through hole 301 as known in the art of the present disclosure, and FIG. 9B illustrates a mounting of a plan-specific instrument template 40 onto a top surface of large ultrasound array 300 whereby instrument trajectories extend through the through hole 301 large ultrasound array 300. This exemplary embodiment provides for a real-time guidance and safe means for instrument insertion, especially when clinical site is under respiratory motion Referring to FIGS. 1-9, those having ordinary skill in the art of the present disclosure will appreciate numerous benefits of the inventions of the present disclosure including, but not limited to, a configurable instrument guide supporting a more accurate intervention instrument insertion into a surgical site as compared to non-configurable instrument guides as known in the art of the present disclosure.

Further, as one having ordinary skill in the art will appreciate in view of the teachings provided herein, structures, elements, components, etc. described in the present disclosure/specification and/or depicted in the Figures may be implemented in various combinations of hardware and software, and provide functions which may be combined in a single element or multiple elements. For example, the functions of the various structures, elements, components, etc. shown/illustrated/depicted in the Figures can be provided through the use of dedicated hardware as well as hardware capable of executing software in association with appropriate software for added functionality. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having described preferred and exemplary embodiments of the various and numerous inventions of the present disclosure (which embodiments are intended to be illustrative and not limiting), it is noted that modifications and variations can be made by persons skilled in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device/system or such as may be used/implemented in/with a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A system for generating a plan-specific instrument template for a percutaneous intervention, the system comprising:
an intervention guide base;
a generic instrument template comprising a geometric representation, the generic instrument template including a generic platform and at least one generic instrument guide formed in and extending through the generic platform, each of the at least one generic instrument guide is i) relocatable, reorientable, and reconfigurable relative to the generic platform and ii) has a generic location, a generic orientation, and a generic configuration relative to the generic platform; and
a controller for generating the plan-specific instrument template for guiding at least one intervention instrument during the percutaneous intervention, the controller comprising:
a processor, and
memory comprising instructions which, when executed by the processor, cause the processor to:
obtain an image segmentation of the intervention guide base,
generate the generic instrument template relative to the image segmentation of the intervention guide base,
obtain a treatment plan including an instrument trajectory for each of the at least one intervention instrument through the instrument guide base, and
at least one of relocate, reorient, and reconfigure the at least one generic instrument guide relative to the generic platform in the generic instrument template to correspond to the instrument trajectory for each of the at least one interventional instrument to generate the plan-specific instrument template.

2. The system of claim 1, wherein the instructions, when executed by the processor, further cause the processor to:
obtain a volumetric image dataset informative of the image of the intervention guide base.

3. The system of claim 1, wherein the instructions, when executed by the processor, further cause the processor to:
at least one of obtain and store a generic instrument template dataset for generating the generic instrument template.

4. The system of claim 1, wherein the instructions, when executed by the processor, further cause the processor to:
control a delineation of at least one instrument trajectory sequentially extending through the generic instrument guide and the image segmentation of the intervention guide base in accordance with the treatment plan.

5. The system of claim 4, wherein the instructions, when executed by the processor, further cause the processor to:
control at least one of the relocation, the reorientation, and the reconfiguration of the generic instrument guide relative to the generic platform of the generic instrument template based on the at least one delineated instrument trajectory.

6. The system of claim 1, wherein the instructions, when executed by the processor, further cause the processor to:
elastically deform a geometric configuration of the generic platform of the generic instrument template to correspond to a geometric configuration of the image segmentation of intervention guide base.

7. The system of claim 4, wherein the instructions, when executed by the processor, further cause the processor to:
output a plan-specific instrument template dataset for at least one of an additive manufacturing and a subtractive manufacturing of the plan-specific instrument template.

8. The system of claim 4, wherein the instrument guide design controller is installed in one of an application server or a workstation.

9. A controller for generating a plan-specific instrument template for a percutaneous intervention, the controller comprising:
a processor, and
a memory comprising instructions which, when executed by the processor, cause the processor to:
obtain an image segmentation of the intervention guide base,
generate a generic instrument template of an intervention guide base relative to the image segmentation of the intervention guide base,
wherein the generic instrument template is a geometric representation,
wherein the generic instrument template including a generic platform and at least one generic instrument guide formed in and extending through the generic platform,
wherein each of the at least one generic instrument guide of the generic instrument template has a generic location and a generic orientation of a generic configuration relative to the platform of the generic instrument template;
obtain a treatment plan including an instrument trajectory for each of the at least one intervention instrument through the instrument guide base; and
at least one of relocate, reorient, and reconfigure the at least one generic instrument guide relative to the generic platform in the generic instrument template to correspond to the instrument trajectory for each of the at least one interventional instrument to generate the plan-specific instrument template.

10. The controller of claim 9, wherein the instructions, when executed by the processor, further cause the processor to:
obtain a volumetric image dataset informative of the image of the intervention guide base.

11. The controller of claim 9, wherein the instructions, when executed by the processor, further cause the processor to:
at least one of obtain and store a generic instrument template dataset for generating the generic instrument template.

12. The controller of claim 9, wherein the instructions, when executed by the processor, further cause the processor to:
control a delineation of at least one instrument trajectory sequentially extending through the generic instrument guide and the image segmentation of the intervention guide base in accordance with the treatment plan.

13. The controller of claim 12, wherein the instructions, when executed by the processor, further cause the processor to:
control at least one of the relocation, the reorientation, and the reconfiguration of the generic instrument guide of the at least one generic instrument guide relative to the generic platform of the generic instrument template based on the at least one delineated instrument trajectory.

14. The controller of claim 9, wherein the instructions, when executed by the processor, further cause the processor to:
  elastically deform a geometric configuration of the generic platform of the generic instrument template to correspond to a geometric configuration of the image segmentation of the intervention guide base.

15. The controller of claim 9, wherein the instructions, when executed by the processor, further cause the processor to:
  output a plan-specific instrument template dataset for at least one of an additive manufacturing and a subtractive manufacturing of the plan-specific instrument template.

* * * * *